United States Patent

Ohwaki et al.

[11] Patent Number: 6,048,882
[45] Date of Patent: Apr. 11, 2000

[54] PROPHYLACTIC AND THERAPEUTIC AGENT FOR HEPATIC DISEASES

[75] Inventors: Tatsuya Ohwaki; Masako Yamada; Hiroyuki Yamazaki; Hitoshi Inoue, all of Iruma-gun; Yoshiyuki Tahara, Ueda; Shigeo Kawase, Iruma-gun, all of Japan

[73] Assignee: Nisshin Flour Milling Co., Ltd., Tokyo, Japan

[21] Appl. No.: 08/875,759

[22] PCT Filed: Feb. 7, 1996

[86] PCT No.: PCT/JP96/00255

§ 371 Date: Aug. 8, 1997

§ 102(e) Date: Aug. 8, 1997

[87] PCT Pub. No.: WO96/24575

PCT Pub. Date: Aug. 15, 1996

[30] Foreign Application Priority Data

Feb. 8, 1995 [JP] Japan .................................. 7-020237

[51] Int. Cl.[7] ...................... C07D 213/38; C07D 317/58; A61K 31/34; A61K 31/36
[52] U.S. Cl. .......................... 514/357; 514/438; 514/456; 514/471; 514/649; 546/329; 549/74; 549/305; 549/492; 564/305
[58] Field of Search .............................. 546/329; 549/74, 549/305, 492; 564/305; 514/357, 438, 456, 471, 649

[56] References Cited

FOREIGN PATENT DOCUMENTS

| | | |
|---|---|---|
| 2 505 826 | 11/1982 | France . |
| 2 338 819 | 2/1974 | Germany . |
| 57-192342 | 11/1982 | Japan . |
| 1-43740 | 9/1987 | Japan . |
| 62-53502 | 11/1987 | Japan . |
| 1 403 851 | 8/1975 | United Kingdom . |
| WO 91/11994 | 8/1991 | WIPO . |

*Primary Examiner*—Zinna Northington Davis
*Attorney, Agent, or Firm*—Oblon, Spivak, McClelland, Maier & Neustadt, P.C.

[57] ABSTRACT

Hepatic diseases can be prevented or treated by administering an isoprenylamine derivative represented by the general formula (II)

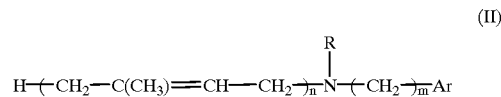

[wherein n represents an integer of 4–12, m represents an integer of 0–3, Ar represents a phenyl group, a furyl group, a thienyl group or a pyridyl group, said group being optionally substituted with one or more of an alkyl group of 1–4 carbon atoms, and alkoxy group of 1–4 carbon atoms, a methylenedioxy group, a hydroxy group or a halogen atom, and R represents a hydrogen atom or an alkyl group of 1–4 carbon atoms] or a pharmacologically acceptable salt thereof at a daily dose of 0.01–500 μg/kg.

A lipid emulsion of the compound (II) is particularly useful and can be administered at a remarkably lowered dose as compared with other pharmaceutical preparations.

30 Claims, No Drawings

PROPHYLACTIC AND THERAPEUTIC AGENT FOR HEPATIC DISEASES

This application is a National Stage Application of PCT/JP96/00255, filed on Feb. 7, 1996.

TECHNICAL FIELD

This invention relates to an isoprenylamine derivative, a lipid emulsion containing the isoprenylamine derivative, a prophylactic and therapeutic agent for hepatic diseases containing an isoprenylamine derivative as an active ingredient and a prophylactic and therapeutic method for hepatic diseases by administering the isoprenylamine derivative.

BACKGROUND ART

Liver may be affected by various pathogenic causes such as viruses, alcohols, chemical substances and undernutrition, whereby hepatic diseases such as acute hepatitis, chronic hepatitis, fatty liver and cirrhosis could be caused. Because there are various pathogenic mechanisms of the development of hepatic diseases and because there are many unknown points involved, a development of a prophylactic and therapeutic agent for hepatic diseases is extremely difficult at present. Presently, the representative drug widely used for the therapy and prophylaxis of hepatic diseases and clinically appreciated includes a glycyrrhizin preparation. However, an efficacy of the glycyrrhizin preparation is not so potent that it should be administered in a large volume through an intravenous drip infusion to develop a certain level of its efficacy. This is disadvantageous because a very heavy burden is imposed on both patients and physicians. Moreover, the glycyrrhizin preparation offers a problem that it has steroid-like side effects, and it is reported that the development rate of the side effects tends to increase when the drug is administered in a large amount.

Under these circumstances, there has been earnestly desired a development of a superior drug which may exert a remarkable inhibitory action against hepatopathy in a smaller amount with a higher safety.

Publicly known are the isoprenylamine derivatives having the general formula (III)

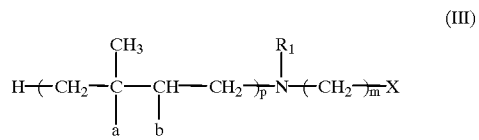

(III)

[wherein p represents an integer of 2–10, a and b represent a hydrogen atom or jointly form a bond between a and b, m represents an integer of 0–4, $R_1$ represents a hydrogen atom, and X represents a phenyl group optionally having a substituent on the nucleus] and a pharmacologically acceptable salt thereof, as disclosed, for instance, in Japanese Patent Kokai No. 192342/1982 (corresponding to U.S. Pat. No. 4,514,573) and others.

The isoprenylamine derivatives having the general formula (III) wherein p is 9, a and b jointly form a bond between a and b, m is an integer of 0–2, $R_1$ represents a hydrogen atom, a lower alkyl group or a nonaprenyl group and X is a phenyl group and pharmacologically acceptable salts thereof are also publicly known and disclosed, for instance, in Japanese Patent Publication No. 53502/1987 (corresponding to U.S. Pat. No. 4,322,555) and others.

Further, the isoprenylamine derivatives having the general formula (III) wherein p is 9 or 10, a and b jointly form a bond between a and b, m is an integer of 1–3, $R_1$ represents a hydrogen atom, a nonaprenyl group or a decaprenyl group and X is an optionally substituted heterocyclic group and pharmacologically acceptable salts thereof are also publicly known and disclosed, for instance, in Japanese Patent Publication No. 43740/1989 and others.

It is said that these isoprenylamine derivatives have an in vivo inducing action of the interferon which has been currently used for the therapy of viral chronic active hepatitis, and also have an antiviral activity derived from the said action.

However, there have not yet been known the isoprenylamine derivatives having the undermentioned general formula (II) wherein n is 11 or more.

DISCLOSURE OF THE INVENTION

The present inventors have made searches and studies to develop a prophylactic or therapeutic agent for hepatic diseases which is free from the aforesaid problems and, as a result, found that the isoprenylamine derivatives of this invention and the lipid emulsion containing the same can exert a remarkable inhibiting action on hepatopathy at a lower dose, upon which this invention has been completed.

A part of the present isoprenylamine derivatives is publicly known as explained above and is known to have an antiviral activity. However, the inhibitory action on hepatopathy of the present isoprenylamine derivatives was observed at a 1/100 or less dose than that for the above antiviral action, and as for the lipid emulsion containing the said isoprenylamine derivatives it was observed at a 1/10000 or less dose than that for the above antiviral action. In addition, there has not yet been reported any invention relating to the lipid emulsion containing the present isoprenylamine derivatives and to a prophylactic or therapeutic agent for hepatic diseases comprising the said lipid emulsion. Moreover, interferon has been currently used as a therapeutic agent for viral chronic active hepatitis, whereas the present isoprenylamine derivatives and the lipid emulsion containing the same can be expected to be effective not only on viral chronic active hepatitis, but also on a wide variety of hepatopathies and hepatic diseases such as chronic persistent hepatitis, alcoholic hepatopathy, fatty liver, cirrhosis, drug-induced hepatopathy and hepatic insufficiency.

This invention will be more fully explained below.

This invention is directed to an isoprenylamine derivative represented by the general formula (I)

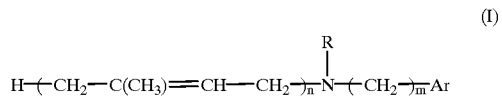

(I)

[wherein n' represents an integer of 11–12, m represents an integer of 0–3, Ar represents a phenyl, furyl, thienyl or pyridyl group optionally substituted by one or more of an alkyl group of 1–4 carbon atoms, an alkoxy group of 1–4 carbon atoms, a methylenedioxy group, a hydroxy group or a halogen atom, and R represents a hydrogen atom or an alkyl group of 1–4 carbon atoms] or a pharmacologically acceptable salt thereof, and to a lipid emulsion comprising an isoprenylamine derivative represented by the general formula (II)

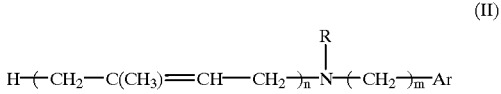

[wherein m, Ar and R have the same meanings as above and n represents an integer of 4–12] or a pharmacologically acceptable salt thereof, as well as a prophylactic or therapeutic agent for hepatic diseases comprising the isoprenylamine derivative and a prophylactic or therapeutic method by administering the isoprenylamine derivative.

In the above general formula (I) or (II), examples of the alkyl group of 1–4 carbon atoms include a methyl, ethyl, n-propyl, isopropyl, n-butyl, isobutyl, sec-butyl or tert-butyl group, and examples of the alkoxy group of 1–4 carbon atoms include a me-thoxy, ethoxy, n-propoxy, isopropoxy, n-butoxy, isobutoxy, sec-butoxy or tert-butoxy group.

In the general formula (I) or (II), Ar represents a phenyl group, a furyl group, a thienyl group or a pyridiyl group, which may be substituted with one or more substituents selected from an alkyl group of 1–4 carbon atoms, an alkoxy group of 1–4 carbon atoms, a methylenedioxy group, a hydroxy group or a halogen atom. When two or more of the said substituents are present, they may be the same or different each other. Examples of the halogen atom include chlorine and bromine. Preferable examples of Ar include a furyl group, a thienyl group, a pyridyl group, a 3,4-methylenedioxyphenyl group and a phenyl group unsubstituted or substituted with 1–5 of the above alkyl group, alkoxy group, hydroxy group or halogen atom.

The compounds of the general formula (II) wherein n is 9, 10 or 11 are particularly preferable. The compounds of the general formula (II) wherein n is 9, 10 or 11, R is a hydrogen atom or a methyl group, Ar is a phenyl group, a 3,4-methylenedioxyphenyl group, 3,4-dihydroxyphenyl group or a 4-hydroxy-3-methoxyphenyl group are particularly preferable.

The isoprenylamine derivatives of the invention represented by the general formula (II) can be prepared according to the process as disclosed in the above-cited Japanese Patent Kokai No. 192342/1982 and others.

They may be prepared, for example, by converting, using a known method, an isoprenyl alcohol represented by the general formula (IV)

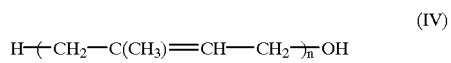

[wherein n has the same meaning as above] (for example, geranylgeraniol, solanesol or dodecaprenol) to the corresponding halide such as geranylgeranyl bromide, solanesyl bromide, decaprenyl bromide, undecaprenyl bromide or dodecaprenyl bromide or the corresponding arylsulfonic acid esters such as geranylgeranyl tosylate, solanesyl tosylate or decaprenyl tosylate, which are then reacted with an amino compound represented by the general formula (V)

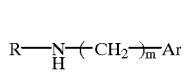

[wherein m, Ar and R have the same meanings as above] in the presence or absence of a base.

The preferable solvents which are used for the reaction include ordinary solvents such as methanol, ethanol, chloroform, tetrahydrofuran (hereinafter referred to as "THF"), ethyl acetate and others. The reaction temperature is in the range of from room temperature to a boiling point of the solvent employed. After completion of the reaction, the reaction mixture may be isolated and purified using any conventional means such as extraction, concentration, column chromatography or crystallization to afford the desired isoprenylamine derivatives.

The compounds of the general formula (II) wherein R is a hydrogen atom can be also prepared according to an alternative process wherein the said halide or arylsulfonic acid ester is reacted with a compound represented by the general formula (VI)

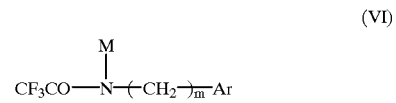

[wherein m and Ar have the same meanings as above and M represents an alkali metal atom], followed by saponification.

This reaction is usually carried out in an aprotic solvent. The preferable solvents which may be used in this reaction include THF, N,N-dimethylformamide (hereinafter referred to as "DMF") and others. The reaction temperature may be in the range of from room temperature to a boiling point of the solvent employed.

As saponification conditions, it is suitable to heat in the presence of an alkali such as potassium hydroxide, sodium hydroxide, ammonia or the like using an alcoholic solvent such as methanol, ethanol or the like in the range of from room temperature to about 80° C. After completion of the reaction, the reaction mixture may be isolated and purified using any conventional means such as extraction, concentration, column chromatography, crystallization and others to obtain the desired isoprenylamine derivative.

Alternatively, the compounds of the general formula (II) wherein R is a hydrogen atom can be prepared by a process which comprises conversion of the compounds of the general formula (IV) to the corresponding amine compounds such as geranylgeranylamine, solanesylamine, decaprenylamine, undecaprenylamine or dodecaprenylamine in a known manner, subsequent dehydrating condensation with an aldehyde compound represented by the general formula (VII)

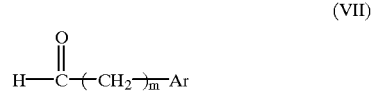

[wherein m and Ar have the same meanings as above] such as benzaldehyde, veratraldehyde, piperonal or the like to form the corresponding imino compounds and subsequent reduction of the imino group of the resulting imino compounds with a suitable reducing agent such as sodium borohydride or lithium aluminum hydride.

Preferable solvents which may be employed in the reaction include ordinary solvents such as methanol, ethanol, chloroform, THF, ethyl acetate or toluene alone or in admixture therewith.

The reaction may be carried out in the temperature range of from room temperature to a boiling point of the solvent. After completion of the reaction, the reaction mixture may be isolated and purified using any conventional means such as extraction, concentration, column chromatography, crystallization and others to obtain the desired isoprenylamine derivative.

The pharmacologically acceptable salts of the isoprenylamine derivatives represented by the general formulae (I) and (II) of this invention include those salts with conventional acids such as mineral acids e.g. hydrochloric acid, sulfuric acid, phosphoric acid, hydrobromic acid, organic acids e.g. acetic acid, oxalic acid, succinic acid, citric acid, maleic acid, malic acid, fumaric acid, tartaric acid, picric acid, methanesulfonic acid, ethanesulfonic acid, acidic amino acids e.g. glutamic acid, aspartic acid.

The present isoprenylamine derivatives of the general formula (I), the present prophylactic and therapeutic agents for hepatic diseases which comprise as an active ingredient the isoprenylamine derivatives of the general formula (II) and the present prophylactic and therapeutic agents for hepatic diseases which comprise a lipid emulsion containing the said isoprenylamine derivatives are useful for prophylaxis of a wide variety of hepatic diseases and hepatopathies, namely, acute hepatitis, chronic hepatitis, fulminant hepatitis, alcoholic hepatopathy, drug-induced hepatopathyl or cirrhosis and hepatic insufficiency as well as for the protection of liver after surgical operation and others.

The present isoprenylamine derivatives and pharmacologically acceptable salts thereof are administered orally or parenterally, preferably via parenteral route. Parenteral administration include subcutaneous, intramuscular or intravenous injection or intrarectal administration or dermal administration.

Pharmaceutical preparations for administration may be prepared in any conventional manner. Preparations for oral administration can be prepared, for example, in the form of tablets, powders, granules, hard capsules, soft capsules or liquid preparations, while preparations for parenteral administration can be in the form of, for example, injections, suppositories, ointments, plasters and the like.

The tablets and capsules for oral administration include conventional components such as binders e.g. dextrin, hydroxypropylcellulose, hydroxypropylmethylcellulose, polyvinylpyrrolidone or macrogol; excipients e.g. lactose, corn starch, calcium phosphate, magnesium aluminate metasilicate; lubricants e.g. calcium stearate or talc; disintegrators e.g. carboxymethylcellulose or crystalline cellulose. These preparations may be coated in a conventional manner well-known in the art.

Liquid preparations for oral administration may be either aqueous or oily suspensions, emulsions, solutions, syrups, elixirs and others or dried products capable of being redissolved in water or any other suitable vehicles before use. Such liquid preparations may contain conventional additives such as suspending agents e.g. sorbitol syrup, carboxymethylcellulose, gelatin, hydroxyethylcellulose, aluminum stearate gel, hydrogenated edible oils and fats; emulsifying agents e.g. lecithin, glyceryl monostearate, acacia; nonaqueous vehicles e.g. palm oil, propylene glycol, ethyl alcohol; preservatives e.g. ethyl p-hydroxybenzoate or sorbic acid.

When administered in the form of injections, the present isoprenylamine derivatives or pharmacologically acceptable salts thereof may be formulated into an oily solution, an aqueous solution, an emulsion or a lipid emulsion as done in the present invention, optionally with emulsifying agents or stabilizers commonly employed in the art.

When the present isoprenylamine derivatives and/or pharmacologically acceptable salts thereof are administered in the form of suppositories, they can be prepared according to a conventional method using lipophilic bases such as cacao butter and Witepsol or hydrophilic bases such as polyethylene glycol, or alternatively they can be applied in the form of rectal capsules wherein a mixture of polyethylene glycol, sesame oil, peanut oil, germ oil, fractionated coconut oil and the like is wrapped in a gelatin sheet. Rectal capsules may be coated, if necessary, with waxy materials.

A dose of the present isoprenylamine drivatives or pharmacologically acceptable salts thereof may vary depending upon the age, sexuality and symptoms of patients and the administration route and, where other formulations than the lipid emulsion are applied, the dose in the parenteral administration may be in the range of 0.5–500 $\mu$g/kg, preferably 5–500 $\mu$g/kg once or in 2–4 divided forms daily.

The present lipid emulsion can be prepared by incorporating the present isoprenylamine derivative of the general formula (II) into fatty particles of a conventional lipid emulsion. It may be readily prepared, for example, by dissolving or dispersing the isoprenylamine derivative of the general formula (II) in a lipid emulsion base and further dispersing the mixture into water using an emulsifying agent to form an oil-in-water emulsion.

The lipid emulsion bases which can be used in preparing the present lipid emulsion include any pharmaceutically acceptable fats and oils conventionally employed in preparing lipid emulsions, for example, vegetable oils such as soybean oil, cotton seed oil, rapeseed oil, peanut oil, safflower oil, corn oil, rice bran oil, sunflower oil; triglycerides of medium chain fatty acids having 8–12 carbon atoms, usually referred to simply as MCT, such as caprylic acid, capric acid, myristic acid, palmitic acid; mono- or di-glycerides of aliphatic acid having 6–18 carbon atoms such as caproic acid, capric acid, myristic acid, palmitic acid, stearic acid, oleic acid, linolic acid, linoleic acid, which may be applied alone or in any combination therewith.

Among these vegetable oils, soybean oil, cotton seed oil, rape seed oil, safflower oil and the like are preferably employed and soybean oil is more preferred. These oils are preferably used in their purified forms and those of a higher purity obtained by further purification by steam distillation are more preferably used.

As the emulsifying agents with which the said lipid emulsion base can be dispersed stably into water, there is used at least one emulsifying agent selected from a physiologically acceptable phospholipid and a nonionic surfactant.

The physiologically acceptable phospholipid includes egg yolk phospholipid, soybean phospholipid, phosphatidyl choline, and the nonionic surfactant includes polyoxyalkylene copolymers (such as polyoxyethylenepolyoxyalkylene derivatives having an average molecular weight of 1000–20000, for example, a hardened castor oil polyoxyethylene-(40)-ether or hardened castor oil polyoxyethylene-(20)-ether). Such emulsifying agents may be employed each alone or together with two or more thereof.

Water which is used as a dispersion medium in preparing the present lipid emulsion may be distilled water or ion-exchanged water in a suitable amount, optionally in admixture with a small amount of a water-miscible organic solvent such as ethanol.

The present lipid emulsion may further include additives, as usually done, such as isotonic agents or stabilizers, if required. The isotonic agents which can be incorporated include, for example, glycerol; a sugar alcohol such as sorbitol or xylitol; a monosaccharide such as glucose or fructose; a disaccharide such as maltose; an amino acid such as L-alanine, L-valine or glycine, among which one or more are suitably selected for use.

These isotonic agents are added to adjust the osmotic pressure of the lipid emulsion to be approximately isotonic with that of body fluid.

The emulsifying aids or co-emulsifying agents which can be suitably incorporated include, for example, aliphatic acids having 6–22 carbon atoms, such as stearic acid, palmitic acid, linolic acid, linolenic acid and salts thereof (such as sodium salts or potassium salts), phosphatidylethanolamine, phosphatidylserine and stearylamine.

Stabilizers which can be used include cholesterol, tocopherol and phosphatidic acid. Albumin and aliphatic acid amide derivatives thereof, as well as polysaccharides and aliphatic acid ester derivatives thereof can also be used as the stabilizer. Albumin used for preparing a drug for human is desirably the human-derived albumin from the standpoint of antigenicity, and the aliphatic acid amide derivatives thereof include those wherein 5–40% of all amino groups present in albumin are amidated with an aliphatic acid having 14–18 carbon atoms such as palmitic acid or stearic acid. On the other hand, the polysaccharides include dextran, pullulan, hydroxyethylstarch, and the aliphatic acid ester derivatives thereof include those wherein 5–40% of all hydroxy groups present in the said polysaccharide are esterified with an aliphatic acid having 14–18 carbon atoms such as palmitic acid or stearic acid.

The present lipid emulsion comprises the isoprenylamine derivative having the general formula (II) or a pharmacologically acceptable salt thereof in an amount of 0.0001–1% (w/v), preferably 0.001–0.1% (w/v), the lipid emulsion base in an amount of 5–50% (w/v), preferably 1–20% (w/v) and emulsifying agent in an amount of 0.05–25% (w/v), preferably 0.5–5% (w/v), with water being added so as to make up a total volume of 100%.

And, if required, there may be added an emulsifying aid [for example, an amount of up to 0.3% (w/v) of an aliphatic acid having 6–22 carbon atoms, preferably 12–20 carbon atoms, or a pharmacologically acceptable salt thereof], and a stabilizer (for example, an amount of not more than 1.2% (w/v), preferably 0.2–0.4% (w/v), of a cholesterol, an amount of not more than 2.5% (w/v), preferably 0.2–0.8% (w/v), of tocopherol or an amount of not more than 5% (w/v), preferably not more than 1% (w/v), of phosphatidic acid, 0.02–5% (w/v), preferably 0.2–2.5% (w/v), of albumin and an aliphatic acid amide derivative thereof and a polysaccharide and an aliphatic acid ester derivative thereof].

The present lipid emulsion can be prepared according to an emulsification procedure known per se. In this instance, a conventional homogenizer may be used as an emulsifier, but it is convenient to use two sorts of homogenizers for preparing a stable and fine lipid emulsion. Illustratively, the present lipid emulsion may be prepared, for example, by dissolving and mixing a given amount of the isoprenylamine derivative of the general formula (II) in the lipid emulsion base such as soybean oil while heating suitably, adding to the mixture a given amount of an emulsifying agent such as purified egg yolk phospholipid and, if necessary, other additives such as emulsifying aids, stabilizers or isotonic agents, warming while stirring to form a uniform mixture, then adding water, treating by a homogenizer to form an oil-in-water crude emulsion and then further homogenizing the resulting emulsion by means of a high pressure homogenizer such as Manton-Gaulin homogenizer or a microfluidics homogenizer. It is also feasible to add the stabilizer and isotonic agent to the resultant lipid emulsion.

In general, the above emulsification procedure may be preferably carried out until an average particle diameter of the dispersed fatty particles in the resulting lipid emulsion reaches to approximately not more than 1 μm, preferably not more than 0.3 μm.

The present lipid emulsion prepared as described above may be freeze-dried as required and the powders obtained by freeze-drying can be reconstituted to the original lipid emulsion upon redissolving in water. Thus, it should be understood that the "lipid emulsion" as used herein is meant to include the freeze-dried products.

When the present isoprenylamine derivatives or pharmacologically acceptable salts thereof are incorporated as an active ingredient into the lipid emulsion, it may be administered in the range of about 0.01–100 μg/kg, preferably 0.1–30 μg/kg, once or in 2–4 divided doses daily depending upon the age, sexuality and symptoms of patients and the administration route. The lipid emulsion is usually administered parenterally by injection, preferably by intravenous injection.

BEST MODE FOR PRACTICING THE INVENTION

The preparative examples of the isoprenylamine derivatives of this invention will be given below.

PREPARATION EXAMPLE 1

N-Geranylgeranylpiperonylamine Hydrochloride

In 200 ml of THF was dissolved 20.5 g of geranylgeranyl bromide, 14.4 ml of piperonylamine was added and stirred at room temperature for one hour. To the reaction mixture was added water and extracted with ethyl acetate. The extract was washed with water and then brine, dried over magnesium sulfate and then concentrated. The concentrate was purified by silica gel column chromatography (using as a developing solvent hexane-ethyl acetate (4:1)→ethyl acetate) to give 17.6 g of N-geranylgeranylpiperonylamine as a yellow liquid.

$^1$H-NMR (δ value in CDCl$_3$): 1.60(9H,s), 1.62(3H,s), 1.68(3H,s), 1.97–2.11(12H,m), 3.22(2H,d,J=6.4 Hz), 3.69 (2H,s), 5.10–5.13(3H,m), 5.28(1H,t,J=6.4 Hz), 5.93(2H,s), 6.75(2H,s), 6.86(1H,s)

Then, N-geranylgeranylpiperonylamine hydrochloride represented by the following formula (hereinafter referred to as "Compound 1") was obtained by a conventional method.

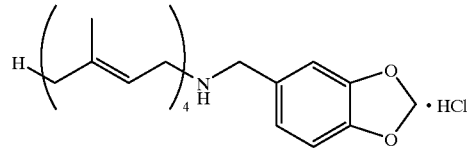

IR(KBr)cm$^{-1}$: 2890, 2778, 1505, 1489, 1473, 1444, 1383, 1251, 1203, 1104, 1048, 987, 929, 894, 814, 774; $^1$H-NMR (δ value in CDCl$_3$): 1.57–1.62(m,12H), 1.68(s,3H), 1.92–2.15(m,12H), 3.40–3.48(m,2H), 3.88–3.94(m,2H), 5.04–5.13(m,3H), 5.43(t,1H,J=6.8 Hz), 5.92(s,2H), 6.79(d, 1H,J=7.8 Hz), 6.99(dd,1H,J=1.5 and 7.8 Hz), 7.08(d,1H,J= 1.5 Hz), 9.75–9.95(m,2H)

PREPARATION EXAMPLE 2

N-Farnesylgeranylpiperonylamine Hydrochloride

In 40 ml of THF was dissolved 7.56 g of piperonylamine, a solution of 2.11 g of farnesylgeranyl bromide in 10 ml of THF was added dropwise at room temperature and stirred at room temperature for 12 hours. Then, the THF was concentrated under reduced pressure. The concentrate was dissolved in chloroform and then washed with a 5% sodium hydroxide solution. After the chloroform layer was concentrated under reduced pressure, the concentrate was dissolved in acetonitrile and extracted with hexane (150 ml×2). The hexane layer was washed with acetonitrile (50 ml×2) and concentrated under reduced pressure. The concentrate was purified by silica gel column chromatography (using ethyl acetate as a developing solvent) to give 2.0 g of N-farnesylgeranylpiperonylamine as a yellow oily substance.

Then, N-farnesylgeranylpiperonylamine hydrochloride represented by the following formula (hereinafter referred to as "Compound 2") was obtained by a conventional method.

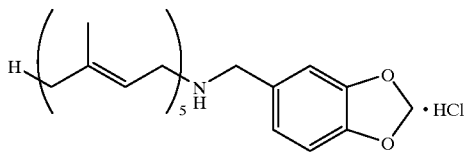

m.p.: 109–112° C.; IR(KBr)cm$^{-1}$: 2856, 1573, 1504, 1489, 1473, 1445, 1384, 1251, 1104, 1048, 982,929, 814, 774; $^1$H-NMR (δ value in CDCl$_3$): 1.60(s,6H), 1.61(s,9H), 1.68(s,3H), 1.93–2.15(m,16H), 3.40–3.48(m,2H), 3.88–3.94(m,2H), 5.05–5.14(m,4H), 5.43(t,1H,J=7.2 Hz), 5.92(s,2H), 6.79(d,1H,J=8.0 Hz), 6.98(dd,1H,J=2.0 and 8.0 Hz), 7.08(d,1H,J=2.0 Hz) 9.82(br.s,2H)

PREPARATIVE EXAMPLE 3

N-Farnesylfarnesylpiperonylamine Hydrochloride

The same procedure as described in Preparative Example 2 was carried out except that 1.96 g of farnesylfarnesyl bromide was used instead of the farnesylgeranyl bromide to give 1.80 g of N-farnesylfarnesylpiperonylamine as a yellow oily substance.

Then, N-farnesylfarnesylpiperonylamine hydrochloride represented by the following formula (hereinafter referred to as "Compound 3") was obtained by a conventional method.

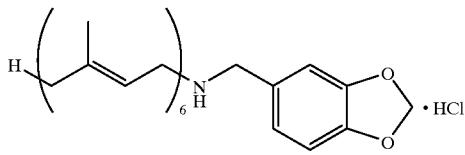

m.p.: 106–110° C.; IR(KBr)cm$^{-1}$: 3450, 2926, 2780, 1574, 1503, 1488, 1445, 1385, 1252, 1104, 1048,981, 930, 814; $^1$H-NMR (δ value in CDCl$_3$): 1.60(s,18H), 1.68(s,3H), 1.93–2.15(m,20H), 3.40–3.48(m,2H), 3.88–3.94(m,2H), 5.05–5.14(m,5H), 5.43(t,1H,J=7.2 Hz), 5.92(s,2H), 6.79(d, 1H,J=8.0 Hz), 6.98(dd,1H,J=2.0 and 8.0 Hz), 7.08(d,1H,J=2.0 Hz), 9.81(br.s,1H)

PREPARATION EXAMPLE 4

N-Farnesylgeranylgeranylpiperonylamine Hydrochloride

In 10 ml of THF was dissolved 4.56 g of farnesylgeranylgeranyl bromide, 3.01 g of piperonylamine was added and stirred at room temperature for one hour. To the reaction mixture was added water and extracted with ethyl acetate. The extract was washed with water and then brine, dried over magnesium sulfate and then concentrated. The concentrate was purified by silica gel column chromatography (using as a developing solvent hexane-ethyl acetate (4:1) →ethyl acetate) to give 1.14 g of N-farnesylgeranylgeranylpiperonylamine as a yellow liquid.

Then, N-farnesylgeranylgeranylpiperonylamine hydrochloride represented by the following formula (hereinafter referred to as "Compound 4") was obtained by a conventional method.

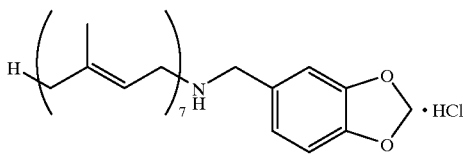

IR(KBr)cm$^{-1}$: 2922, 1505, 1489, 1445, 1383, 1252, 1104, 1047, 985, 929, 813; $^1$H-NMR(δ value in CDCl$_3$): 1.58(s, 3H), 1.60(s,18H), 1.68(s,3H), 1.90–2.15(m,24H), 3.40–3.48(m,2H), 3.88–3.94(m,2H), 5.04–5.15(m,6H), 5.43(t,1H,J=6.8 Hz), 5.92(s,2H), 6.79(d,1H,J=8.0 Hz), 6.98(dd,1H, J=1.5 and 8.0 Hz), 7.08(d,1H,J=1.5 Hz), 9.81(br.s,2H)

PREPARATION EXAMPLE 5

N-Farnesylfarnesylgeranylpiperonylamine Hydrochloride

The same procedure as described in Preparative Example 2 was carried out except that 1.97 g of farnesylfarnesylgeranyl bromide was used instead of the farnesylgeranyl bromide to give 1.32 g of N-farnesylfarnesylgeranylpiperonylamine as a yellow oily substance.

Then, N-farnesylfarnesylgeranylpiperonylamine hydrochloride represented by the following formula (hereinafter referred to as "Compound 5") was obtained by a conventional method.

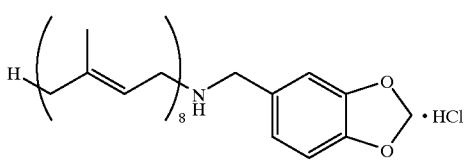

m.p.: 96–99° C.; IR(KBr)cm$^{-1}$: 2856, 2782, 1673, 1574, 1504, 1445, 1384, 1252, 1104, 1048, 980,943, 814, 635; $^1$H-NMR (δ value in CDCl$_3$): 1.60(s,24H), 1.68(s,3H), 1.92–2.16(m,28H), 3.40–3.48(m,2H), 3.91(br.s,2H), 5.05–5.15(m,7H), 5.43(t,1H,J=7.2 Hz), 5.92(s,2H), 6.79(d, 1H,J=8.0 Hz), 6.98(dd,1H,J=2.0 and 8.0 Hz), 7.08(d,1H,J=2.0 Hz), 9.80(br.s,1H)

PREPARATIVE EXAMPLE 6

N-Solanesylpiperonylamine Hydrochloride

In 50 ml of THF was dissolved 20 g of solanesyl bromide, 7.2 ml of piperonylamine was added and stirred at room temperature for one hour. To the reaction mixture was added water and extracted with ethyl acetate. The extract was washed with water and then brine, dried over magnesium sulfate and then concentrated. The concentrate was purified by silica gel column chromatography (using as a developing solvent hexane-ethyl acetate (4:1)→ethyl acetate) to give 9.2 g of N-solanesylpiperonylamine as a yellow liquid.

$^1$H-NMR (δ value in CDCl$_3$): 1.60(24H,s), 1.61(3H,s), 1.68(3H,s), 1.96–2.12(32H,m), 3.22(2H,d,J=6.4 Hz), 3.69 (2H,s), 5.10–5.13(8H,m), 5.28(1H,t,J=6.4 Hz), 5.93(2H,s), 6.75(2H,s), 6.83(1H,s)

In 15 ml of acetone was dissolved 3.0 g of the N-solanesylpiperonylamine obtained according to the above procedure, the solution was made slightly acidic by the addition of a hydrogen chloride-ether solution and allowed to stand in a refrigerator overnight. The crystals thus separated out were recovered by filtration and dried to give 2.0 g of N-solanesylpiperonylamine hydrochloride of the following formula (hereinafter referred to as "Compound 6") as white crystals.

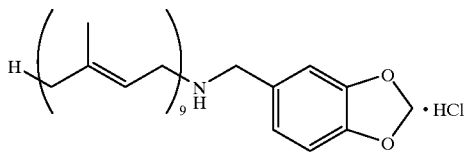

m.p.: 97.1–98.0° C.; $^1$H-NMR (δ value in CDCl$_3$): 1.60 (24H,s), 1.61(3H,s), 1.68(3H,s), 1.97–2.14(32H,m), 3.44 (2H,dJ=6.8 Hz), 3.90(2H,s), 5.08–5.13(8H,m), 5.43(1H,t J=6.8 Hz), 5.93(2H,s), 6.78(1H,d J=7.8 Hz), 6.98(1H,d J=7.8 Hz), 7.08(1H,s), 9.84(2H,bs)

PREPARATION EXAMPLE 7

N-Solanesylbenzylamine Hydrochloride

In 10 ml of THF was dissolved 6.94 g of solanesyl bromide, 2.14 g of benzylamine was added and stirred at room temperature for one hour. To the reaction mixture was added water and extracted with ethyl acetate. The extract was washed with water and then brine, dried over magnesium sulfate and then concentrated. The concentrate was purified by silica gel column chromatography (using as a developing solvent hexane-ethyl acetate (4:1)→ethyl acetate) to give 1.5 g of N-solanesylbenzylamine as a yellow liquid.

Then, N-solanesylbenzylamine hydrochloride represented by the following formula (hereinafter referred to as "Compound 7") was obtained according to a conventional method.

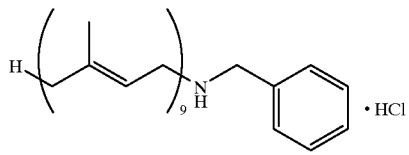

IR(KBr)cm$^{-1}$: 2926, 1499, 1447, 1428, 1385, 982, 876, 799, 748, 697; $^1$H-NMR(δ value in CDCl$_3$): 1.59(s,3H), 1.60(s,24H), 1.68(s,3H), 1.92–2.13(m,32H), 3.38–3.45(m, 2H), 3.95–4.00(m,2H), 5.05–5.14(m,8H), 5.43(t,1H,J=7.0 Hz), 7.30–7.40(m,3H), 7.52–7.57(m,2H), 9.82(br.s,2H)

PREPARATIVE EXAMPLE 8

N-Solanesyl-4-hydroxybenzylamine Hydrochloride

In 20 ml of methanol was dissolved 0.61 g of 4-hydroxybenzaldehyde and 10 ml of a solution of 3.10 g of solanesylamine in chloroform was added dropwise at room temperature. After completion of the dropwise addition, the mixture was stirred at room temperature for 12 hours. To this solution was added portionwise 0.227 g of sodium borohydride at room temperature and stirred for further 3 hours. The reaction mixture was concentrated under reduced pressure, water was added to the concentrate and extracted with chloroform (100 ml×2). The chloroform layer was washed with water and then a saturated aqueous solution of sodium chloride, dried over magnesium sulfate and concentrated under reduced pressure. The concentrate was dissolved in acetonitrile and extracted with hexane (100 ml×2). The hexane layer was washed with acetonitrile, the hexane was distilled off and concentrated and purified by silica gel column chromatography (using ethyl acetate as a developing solvent) to give 1.50 g of N-solanesyl-4-hydroxybenzylamine as a yellow oily substance.

Then, N-solanesyl-4-hydroxybenzylamine hydrochloride represented by the following formula (hereinafter referred to as "Compound 8") was obtained as pale yellow crystals according to a conventional method.

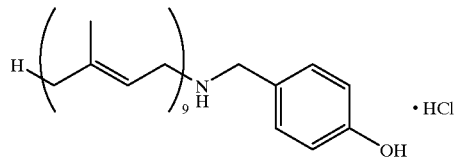

m.p.: 58–64° C.; IR(KBr)cm$^{-1}$: 2962, 2914, 1616, 1521, 1448, 1385, 1266, 1213, 1178, 1108, 877,796; $^1$H-NMR(δ value in CDCl$_3$): 1.50–1.70(m,30H), 1.93–2.20(m,32H), 3.53–3.60(m,2H), 3.84–3.94(m,2H), 5.06–5.15(m,8H), 5.43–5.50(m,1H), 6.75(d,2H,J=8.0 Hz), 7.24(d,2H,J=8.0 Hz), 7.68(br.s,1H), 9.28(br.s,1H)

PREPARATIVE EXAMPLE 9

N-Solanesyl-4-chlorobenzylamine Hydrochloride

The same procedure as described in Preparative Example 8 was carried out except that 0.70 g of 4-chlorobenzaldehyde was used instead of the 4-hydroxybenzaldehyde to give 2.70 g of N-solanesyl-4-chlorobenzylamine as a yellow oily substance.

Then, N-solanesyl-4-chlorobenzylamine hydrochloride represented by the following formula (hereinafter referred to as "Compound 9") was obtained as white crystals according to a conventional method.

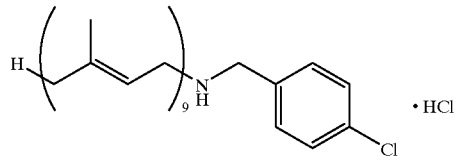

m.p.: 110–124° C.; $^1$H-NMR(δ value in CDCl$_3$): 1.56(s, 3H), 1.60(s,24H), 1.68(s,3H), 1.94–2.14(m,32H), 3.39(d, 2H,J=7.0 Hz), 3.94(s,2H), 5.05–5.15(m,8H), 5.40(t,1H,J= 7.0 Hz), 7.32–7.37(m,2H), 7.48–7.53(m,2H), 9.94(br.s,2H)

PREPARATIVE EXAMPLE 10

N-Solanesyl-4-methylbenzylamine Hydrochloride

The same procedure as described in Preparative Example 8 was carried out except that 0.60 g of p-tolualdehyde was used instead of the 4-hydroxybenzaldehyde to give 3.09 g of N-solanesyl-4-methylbenzylamine as a yellow oily substance.

Then, N-solanesyl-4-methylbenzylamine hydrochloride represented by the following formula (hereinafter referred to as "Compound 10") was obtained as white crystals according to a conventional method.

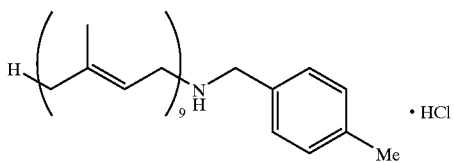

m.p.: 102–108° C.; $^1$H-NMR($\delta$ value in CDCl$_3$): 1.54(s, 3H), 1.60(s,24H), 1.68(s,3H), 1.93–2.13(m,32H), 2.28(s, 3H), 3.35–3.43(m,2H), 3.88–3.94(m,2H), 5.05 5.15(m,8H), 5.42(t,1H,J=7.3 Hz), 7.16(d,2H,J=7.8 Hz), 7.41(d,2H,J=7.8 Hz), 9.82(br.s,2H)

PREPARATIVE EXAMPLE 11

N-Solanesyl-3,4-dihydroxybenzylamine Hydrochloride

The same procedure as described in Preparative Example 8 was carried out except that 1.53 g of 3,4-ditetrahydropyranyloxybenzaldehyde was used instead of the 4-hydroxybenzaldehyde to give 2.30 g of N-solanesyl-3,4-ditetrahydropyranyloxybenzylamine as a yellow oily substance.

Then, the compound was dissolved in acetone and a 4N hydrochloric acid-ethyl acetate solution was added dropwise at room temperature to conduct the deprotection and the formation of hydrochloride concurrently, thereby producing N-solanesyl-3,4-dihydroxybenzylamine hydrochloride represented by the following formula (hereinafter referred to as "Compound 11") as white amorphous solid.

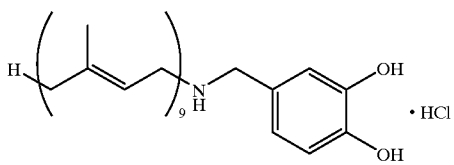

m.p.: 46–48° C.; $^1$H-NMR($\delta$ value in CDCl$_3$): 1.60(s, 24H), 1.67(s,3H), 1.68(s,3H), 1.72–1.85(m,2H), 1.92–2.15 (m,32H), 3.60(br.s,2H), 3.84(br.s,2H), 5.05–5.15(m,8H), 5.43–5.50(m,1H), 6.65–6.80(m,2H), 7.10(s,1H), 8.85(br.s, 2H)

PREPARATIVE EXAMPLE 12

N-Solanesyl-4-hydroxy-3-methoxybenzylamine Hydrochloride

The same procedure as described in Preparative Example 8 was carried out except that 0.76 g of 4-hydroxy-3-methoxybenzaldehyde was used instead of the 4-hydroxybenzaldehyde to give 2.64 g of N-solanesyl-4-hydroxy-3-methoxybenzylamine as a yellow oily substance.

Then, N-solanesyl-4-hydroxy-3-methoxybenzylamine hydrochloride represented by the following formula (hereinafter referred to as "Compound 12") was obtained as white powders according to a conventional method.

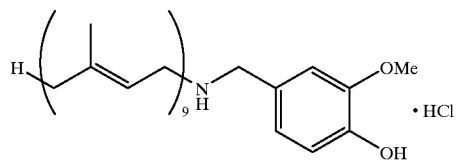

m.p.: 55–60° C.; IR(KBr)cm$^{-1}$: 3425, 2962, 2916, 1605, 1526, 1450, 1384, 1283, 1161, 1131, 1033, 876, 797; $^1$H-NMR($\delta$ value in CDCl$_3$): 1.55(s,3H), 1.60(s,24H), 1.68 (s,3H), 1.93–2.14(m,32H), 3.35–3.43(m,2H), 3.90–3.97(m, 5H), 5.04–5.15(m,8H), 5.41(t,1H,J=7.0 Hz), 5.68(s,2H), 6.81(dd,1H,J=1.5 and 8.0 Hz), 6.85(d,1H,J=8.0 Hz), 7.39(d, 1H,J=1.5 Hz), 9.79(br.s,2H)

PREPARATIVE EXAMPLE 13

N-Solanesylveratrylamine Hydrochloride

In 10 ml of THF was dissolved 6.94 g of solanesyl bromide, 3.34 g of veratrylamine was added and stirred at room temperature for one hour. To the reaction mixture was then added water and extracted with ethyl acetate. The extract was washed with water and then brine, dried over magnesium sulfate and then concentrated. The concentrate was purified by silica gel column chromatography (using as a developing solvent hexane-ethyl acetate (4:1)→ethyl acetate) to give 1.5 g of N-solanesylveratrylamine as a yellow liquid.

Then, N-solanesylveratrylamine hydrochloride represented by the following formula (hereinafter referred to as "Compound 13") was obtained according to a conventional method.

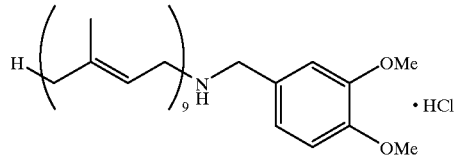

IR(KBr)cm$^{-1}$: 2920, 1612, 1596, 1526, 1453, 1428, 1384, 1271, 1253, 1164, 1143,1038, 1022, 853, 823; $^1$H-NMR ($\delta$ value in CDCl$_3$): 1.55(s,3H), 1.60(s,24H), 1.68(s,3H), 1.93–2.12(m,32H), 3.37–3.43(m,2H), 3.82(s,3H), 3.91–3.95 (m,2H), 3.95(s,3H), 5.05–5.14(m,8H), 5.42(t,1H,J=7.0 Hz), 6.79(d,1H,J=8.0 Hz), 6.93(dd,1H,J=8.0 Hz), 7.34(d,1H,J= 2.0 Hz), 9.83(br.s,2H)

PREPARATIVE EXAMPLE 14

N-Solanesyl-2,3,4,5-tetramethoxy-6-methylbenzylamine Hydrochloride

The same procedure as described in Preparative Example 8 was carried out except that 1.20 g of 2,3,4,5-tetramethoxy-6-methylbenzaldehyde was used instead of the 4-hydroxybenzaldehyde to give 3.80 g of N-solanesyl-2,3,4,5-tetramethoxy-6-methylbenzylamine as a yellow oily substance.

Then, N-solanesyl-2,3,4,5-tetramethoxy-6-methylbenzylamine hydrochloride represented by the following formula (hereinafter referred to as "Compound 14") was obtained as white crystals according to a conventional method.

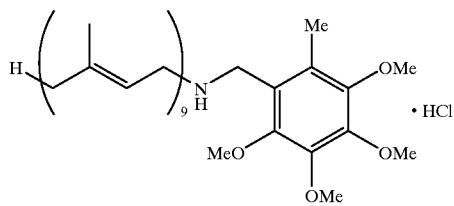

m.p.: 34° C.; IR(KBr)cm$^{-1}$: 3410, 2850, 1575, 1472, 1447, 1410, 1384, 1355, 1270, 1198, 1110, 1052, 979; $^1$H-NMR(δ value in CDCl$_3$): 1.60(s,24H), 1.68(s,3H), 1.68 (s,3H), 1.93–2.14(m,32H), 2.29(s,3H), 3.52–3.60(m,2H), 3.76(s,3H), 3.88(s,3H), 3.92(s,2H), 3.96(s,3H), 4.07–4.12 (m,2H), 5.04–5.15(m,8H), 5.48(t,lH,J=6.8 Hz), 9.16(br.s, 2H)

PREPARATIVE EXAMPLE 15

N-Solanesylpiperonylamine Malate

In 10 ml of ethanol was dissolved 1.8 g of N-solanesylpiperonylamine obtained in Preparative Example 6, 0.47 g of malic acid was added and completely dissolved by heating to 40° C. The reaction mixture was stirred under ice-cooling to separate out crystals. The crystals thus separated out was recovered by filtration and dried to give 1.3 g of N-solanesylpiperonylamine malate represented by the following formula as white crystals (hereinafter referred to as "Compound 15").

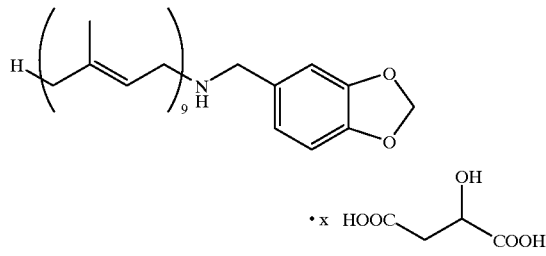

m.p.: 50° C.; $^1$H-NMR(δ value in CDCl$_3$): 1.60(24H,s), 1.62(3H,s), 1.68(3H,s), 1.97–2.09(32H,m), 2.70–2.73(2H, m), 3.52(2H,d J=7.3 Hz), 3.98(2H,s), 4.15–4.19(1H,m), 5.10–5.13(8H,m), 5.41(1H,t J=7.3 Hz), 5.95(2H,s), 6.77 (1H,d J=7.8 Hz), 6.84(1H,d J=7.8 Hz), 6.92(1H,s)

PREPARATIVE EXAMPLE 16

N-Solanesyl-(3,4-methylenedioxy)aniline Hydrochloride

The same procedure as described in Preparative Example 2 was carried out except that 6.86 g of 3,4-methylenedioxyaniline was used instead of the piperonylamine and 3.47 g of solanesyl bromide was used instead of the farnesylgeranyl bromide to give 1.83 g of N-solanesyl-(3,4-methylenedioxy)aniline as white crystals.

Then, N-solanesyl-(3,4-methylenedioxy)aniline hydrochloride represented by the following formula (hereinafter referred to as "Compound 16") was obtained as white crystals according to a conventional method.

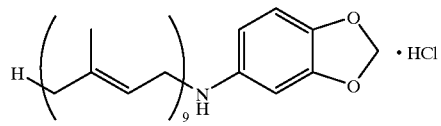

m.p.: 51–53° C.; IR(KBr)cm$^{-1}$: 3435, 2964, 2912, 1506, 1446, 1385, 1259, 1108, 1035, 920, 878, 796; $^1$H-NMR(δ value in CDCl$_3$): 1.48(s,3H), 1.60(s,24H), 1.68(s,3H), 1.92–2.11(m,32H), 3.85(d,1H,J=7.5 Hz), 4.98–5.04(m,1H), 5.06–5.15(m,7H), 5.40(t,1H,J=7.5 Hz), 5.99(s,2H), 6.74–6.78(m,1H), 7.01–7.05(m,2H), 11.33(br.s,2H)

PREPARATIVE EXAMPLE 17

N-Solanesyl-2-(3,4-methylenedioxyphenyl) ethylamine Hydrochloride

The same procedure as described in Preparative Example 2 was carried out except that 1.90 g of 2-(3,4-methylenedioxyphenyl)ethylamine was used instead of the piperonylamine and 6.94 g of solanesyl bromide was used instead of the farnesylgeranyl bromide to give 1.2 g of N-solanesyl-2-(3,4-methylenedioxyphenyl)ethylamine as a yellow oily substance.

Then, N-solanesyl-2-(3,4-methylenedioxyphenyl)-ethylamine hydrochloride represented by the following formula (hereinafter referred to as "Compound 17") was obtained as white crystals according to a conventional method.

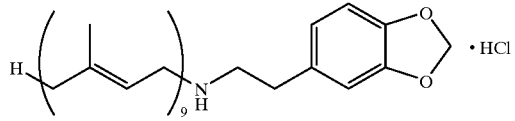

m.p.: 110–114° C.; IR(KBr)cm$^{-1}$: 3420, 2962, 2918, 1505, 1487, 1441, 1385, 1245, 1195, 1153, 1110, 1043, 941, 926, 875, 815, 799; $^1$H-NMR(δ value in CDCl$_3$): 1.57(s,3H), 1.60(s,21H), 1.68(s,3H), 1.70(s,3H), 1.90–2.12(m, 32H), 2.99–3.20(m,4H), 3.59–3.67(m,2H), 4.99–5.15(m,8H), 5.43 (t,1H,J=6.8 Hz), 5.92(s,2H), 6.66–6.75(m,3H), 9.69(br.s, 2H)

PREPARATIVE EXAMPLE 18

N-Solanesyl-3-(3,4-methylenedioxyphenyl) propylamine Hydrochloride

The same procedure as described in Preparative Example 8 was carried out except that 0.70 g of 3-(3,4-methylenedioxyphenyl)propionaldehyde was used instead of the 4-hydroxybenzaldehyde to give 1.09 g of N-solanesyl-3-(3,4-methylenedioxyphenyl)propylamine as a yellow oily substance.

Then, N-solanesyl-3-(3,4-methylenedioxyphenyl) propylamine hydrochloride represented by the following formula (hereinafter referred to as "Compound 18") was obtained as white crystals according to a conventional method.

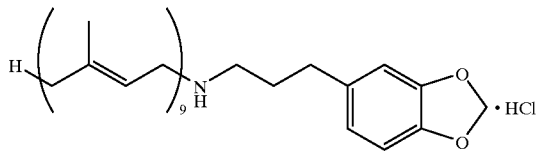

m.p.: 72–75° C.; IR(KBr)cm$^{-1}$: 3394, 2962, 2852, 1505, 1491, 1445, 1384, 1265, 1245, 1103, 1040, 924, 874, 812, 799; $^1$H-NMR(δ value in CDCl$_3$): 1.60(s,24H), 1.67(s,3H), 1.68(s,3H), 1.93–2.18(m,32H), 2.62(t,2H,J=7.3 Hz), 2.77–2.87(m,2H), 3.53–3.60(m,2H), 5.03–5.15(m,8H), 5.38 (t,1H,J=6.8 Hz), 5.89(s,2H), 6.60–6.71(m,3H), 9.56(br.s, 2H)

PREPARATIVE EXAMPLE 19

N-Methyl-N-solanesylpiperonylamine

In 10 ml of THF was suspended 0.3 g of 60% sodium hydride, a solution of 4.0 g of N-solanesylpiperonyl amine in 10 ml of THF was added dropwise while stirring at room temperature. After stirring the mixture at room temperature for 30 minutes, 1.0 ml of methyl iodide was added slowly, followed by stirring at room temperature for 30 minutes. To the reaction mixture was added portionwise water while ice-cooling and stirring and then extracted with chloroform. The extract was washed with water and then brine, dried over magnesium sulfate and then concentrated. The concentrate was purified by silica gel column chromatography (using as a developing solvent hexane-ethyl acetate (9:1)) to give 1.5 g of N-methyl-N-solanesylpiperonylamine represented by the following formula as a yellow liquid (hereinafter referred to as "Compound 19").

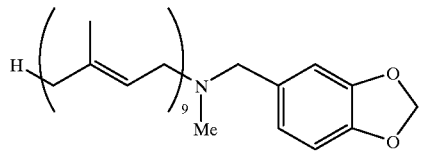

$^1$H-NMR(δ value in CDCl$_3$): 1.60(24H,s), 1.62(3H,s), 1.68(3H,s), 1.96–2.12(32H,m), 2.16(3H,s), 2.96(2H,d J=6.8 Hz), 3.38(2H,s), 5.08–5.13(8H,m), 5.30(1H,t J=6.8 Hz), 5.92(2H,s), 6.73(2H,s), 6.83(1H,s)

PREPARATIVE EXAMPLE 20

N-Decaprenylpiperonylamine Hydrochloride

In 10 ml of THF was dissolved 7.63 g of decaprenyl bromide, 3.01 g of piperonylamine was added and stirred at room temperature for one hour. To the reaction mixture was added water and extracted with ethyl acetate. The extract was washed with water and then brine, dried over magnesium sulfate and then concentrated. The concentrate was purified by silica gel column chromatography (using as a developing solvent hexane-ethyl acetate (4:1)→ethyl acetate) to give 1.5 g of N-decaprenylpiperonylamine as a yellow liquid.

Then, N-decaprenylpiperonylamine hydrochloride represented by the following formula (hereinafter referred to as "Compound 20") was obtained according to a conventional method.

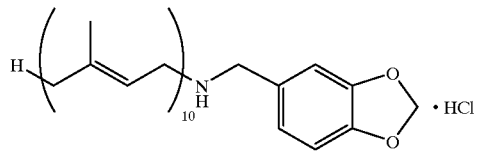

IR(KBr)cm$^{-1}$: 3398, 2924, 1503, 1484, 1444, 1384, 1252, 1048, 929, 875, 813; $^1$H-NMR(δ value in CDCl$_3$): 1.60(s, 30H), 1.68(s,3H), 1.92–2.15(m,36H), 3.40–3.48(m,2H), 3.85–3.95(m,2H), 5.04–5.16(m,9H), 5.43(t,1H,J=7.0 Hz), 5.92(s,2H),6.78(d,1H,J=7.8 Hz), 6.98(dd,1H,J=2.0 and 7.8 Hz), 7.08(d,1H,J=2.0 Hz), 9.82(br.s,2H)

PREPARATIVE EXAMPLE 21

N-Undecaprenylpiperonylamine Hydrochloride

In 10 ml of THF was dissolved 8.30 g of undecaprenyl bromide, 3.01 g of piperonylamine was added and stirred at room temperature for one hour. To the reaction mixture was added water and extracted with ethyl acetate. The extract was washed with water and then brine, dried over magnesium sulfate and then concentrated. The concentrate was purified by silica gel column chromatography (using as a developing solvent hexane-ethyl acetate (4:1)→ethyl acetate) to give 0.2 g of N-undecaprenylpiperonylamine as a yellow liquid.

Then, N-undecaprenylpiperonylamine hydrochloride represented by the following formula (hereinafter referred to as "Compound 21") was obtained according to a conventional method.

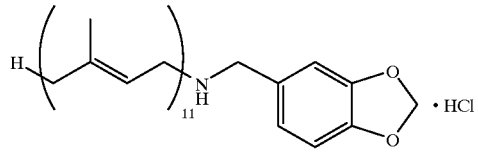

$^1$H-NMR(δ value in CDCl$_3$): 1.60(s,33H), 1.68(s,3H), 1.91–2.14(m,40H), 3.40–3.48(m,2H), 3.86–3.94(m,2H), 5.05–5.15(m,10H), 5.39–5.48(m,1H), 5.90–5.93(m,2H), 6.76–6.81(m,1H), 6.95–7.01(m,1H), 7.06–7.11(m,1H), 9.78 (br.s,2H)

PREPARATIVE EXAMPLE 22

N-Undecaprenyl-3-methoxy-4-hydroxybenzylamine Hydrochloride

The same procedure as described in Preparative Example 8 was carried out except that 0.192 g of 3-methoxy-4-hydroxybenzaldehyde was used instead of the 4-hydroxybenzaldehyde and 1.15 g of undecaprenylamine was used instead of the solanesylamine to give 1.16 g of N-undecaprenyl-3-methoxy-4-hydroxybenzylamine as a yellow oily substance.

$^1$H-NMR(δ value in CDCl$_3$): 1.60(s,30H), 1.62(s,3H), 1.68(s,3H), 1.94–2.13(m,40H), 3.26(d,2H,J=6.8 Hz), 3.73(s, 2H), 3.89(s,3H), 5.06–5.16(m,10H), 5.30(t,1H,J=6.8 Hz), 6.78(dd,1H,J=1.5 and 8.3 Hz), 6.85(d,1H,J=8.3 Hz), 6.92(d, 1H,J=1.5 Hz)

Then, N-undecaprenyl-3-methoxy-4-hydroxybenzylamine hydrochloride represented by the following formula (hereinafter referred to as "Compound 22")

was obtained as pale yellow crystals according to a conventional method.

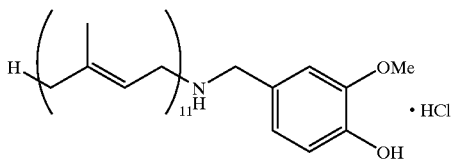

m.p.: 47–49° C.; $^1$H-NMR($\delta$ value in CDCl$_3$): 1.59(s,3H), 1.60(s,30H), 1.68(s,3H), 1.94–2.13(m,40H), 3.35–3.43(m, 2H), 3.92–3.96(m,5H), 5.05–5.15(m,10H), 5.41(t,1H,J=6.8 Hz), 5.67(s,1H), 6.80–6.87(m,2H), 7.38–7.41(m,1H), 9.74–9.90(m,2H)

PREPARATIVE EXAMPLE 23

N-Dodecaprenylpiperonylamine Hydrochloride

The same procedure as described in Preparative Example 2 was carried out except that 2.24 g of dodecaprenyl bromide was used instead of the farnesylgeranyl bromide to give 1.71 g of N-dodecaprenylpiperonylamine as a yellow oily substance.

$^1$H-NMR($\delta$ value in CDCl$_3$): 1.60(s,33H), 1.62(s,3H), 1.68(s,3H), 1.93–2.14(m,44H), 3.22(d, 2H,J=6.8 Hz), 3.69 (s,2H), 5.07–5.15(m,7H), 5.28(t,1H,J=6.8 Hz), 6.75(s,2H), 6.84(s,1H)

Then, N-dodecaprenylpiperonylamine hydrochloride represented by the following formula (hereinafter referred to as "Compound $_{23}$") was obtained according to a conventional method.

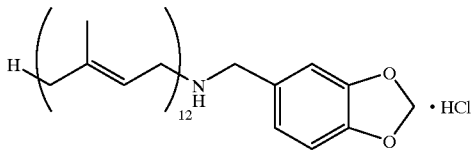

m.p.: 91–93° C.; $^1$H-NMR($\delta$ value in CDCl): 1.60(s, 36H), 1.69(s,3H), 1.93–2.14(m,44H), 3.40–3.48(m,2H), 3.88–3.94(m,2H), 5.05–5.15(m,12H), 5.43(t,1H,J=6.8 Hz), 5.92(s,2H), 6.79(d,1H,J=8.3 Hz), 6.98(dd,1H,J=2.0 and 8.3 Hz), 7.08(d,1H,J=2.0 Hz), 9.75–9.95(m,2H)

PREPARATIVE EXAMPLE 24

N-Solanesyl-2-furfurylamine Hydrochloride

The same procedure as described in Preparative Example 2 was carried out except that 9.71 g of furfuryl amine was used instead of the piperonylamine and 3.47 g of solanesyl bromide was used for the farnesylgeranyl bromide to give 3.00 g of N-solanesyl-2-furfurylamine as a yellow oily substance.

Then, N-solanesyl-2-furfurylamine hydrochloride represented by the following formula (hereinafter referred to as "Compound 24") was obtained according to a conventional method as a pale yellow amorphous solid.

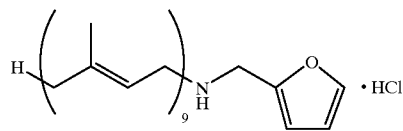

m.p.: 90–94° C.; $^1$H-NMR($\delta$ value in CDCl$_3$): 1.60(s, 24H), 1.65(s,3H),1.68(s,3H), 1.93–2.14(m,32H), 3.50–3.58 (m,2H), 4.10(t,2H,J=4.9 Hz), 5.05–5.15(m,8H), 5.43(t,1H, J=6.8 Hz),6.39(dd,1H,J=2.0 and 3.5 Hz), 6.69(d,1H,J=3.5 Hz), 7.45(d,1H,J=2.0 Hz), 9.93(br.s,2H)

PREPARATIVE EXAMPLE 25

N-Solanesyl-2-thienylamine Hydrochloride

The same procedure as described in Preprative Example 8 was carried out except that 0.67 g of 2-thienylaldehyde was used instead of the 4-hydroxybenzaldehyde to give 2.38 g of N-solanesyl-2-thienylamine as a yellow oily substance.

Then, N-solanesyl-2-thienylamine hydrochloride represented by the following formula (hereinafter referred to as "Compound 25") was obtained according to a conventional method as white crystals.

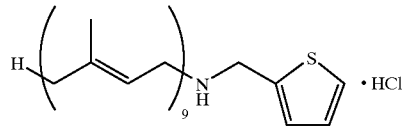

m.p.: 102–105° C.; $^1$H-NMR($\delta$ value in CDCl$_3$): 1.60(s, 24H), 1.62(s,3H), 1.68(s,3H), 1.93–2.14(m,32H), 3.48–3.55 (m,2H), 4.20(br.s,2H), 5.05–5.15(m,8H), 5.43(t,1H,J=6.8 Hz), 7.02(dd,1H,J=3.5 and 5.0 Hz), 7.32(dd,1H,J=1.0 and 5.0 Hz), 7.40(dd,1H,J=1.0 and 3.5 Hz)

PREPARATIVE EXAMPLE 26

N-Solanesyl-3-pyridylmethylamine Dihydrochloride

The same procedure as described in Preparative Example 8 was carried out except that 0.64 g of 3-pyridylaldehyde was used instead of the 4-hydroxybenzaldehyde to give 2.70 g of N-solanesyl-3-pyridylmethylamine as a yellow oily substance.

Then, N-solanesyl-3-pyridylmethylamine dihydrochloride represented by the following formula (hereinafter referred to as "Compound 26") was obtained according to a conventional method as a white amorphous solid.

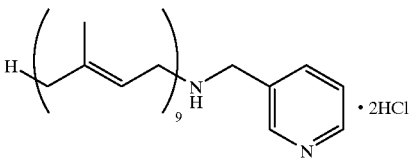

m.p.: 129–135° C.; $^1$H-NMR($\delta$ value in CDCl$_3$): 1.60(s, 24H), 1.68(s,3H), 1.82(s,3H), 1.93–2.17(m,32H), 3.83–3.92 (m,2H), 4.39–4.50(m,2H), 5.05–5.15(m,8H), 5.58(t,1H,J= 7.2 Hz), 8.01(dd,1H,J=6.0 and 8.0 Hz), 8.85(d,1H,J=5.0 Hz), 8.98(d,1H,J=8.0 Hz), 9.62(s,1H), 10.36(br.s,2H)

PREPARATIVE EXAMPLE 27

N-Undecaprenyl-3-pyridylmethylamine Dihydrochloride

The same procedure as described in Preparative Example 8 was carried out except that 0.177 g of 3-pyridylaldehyde was used instead of the 4-hydroxybenzaldehyde and 1.15 g of undecaprenylamine was used instead of the solanesylamine to give 0.65 g of N-undecaprenyl-3-pyridylmethylamine as a yellow oily substance.

$^1$H-NMR(value in CDCl$_3$): 1.60(s,30H), 1.62(s,3H), 1.68 (s,3H), 1.93–2.14(m,40H), 3.24(d,2H,J=6.8 Hz), 3.79(s, 2H), 5.07–5.15(m,10H), 5.28(t,1H,J=6.8 Hz), 7.23–7.28(m, 1H), 7.65–7.72(m,1H), 8.50(dd,1H,J=1.5 and 4.8 Hz), 8.56 (d,1H,J=2.0 Hz)

Then, N-undecaprenyl-3-pyridylmethylamine dihydrochloride represented by the following formula (hereinafter referred -to as "Compound 27") was obtained according to a conventional method as a white amorphous solid.

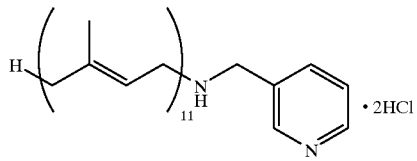

$^1$H-NMR(δ value in CDCl$_3$): 1.60(s,30H), 1.68(s,3H), 1.82(s,3H), 1.93–2.16(m,40H), 3.83–3.92(m,2H), 4.40–4.50 (m,2H), 5.05–5.15(m,10H), 5.58(t,1H,J=6.8 Hz), 7.98–8.06 (m,1H), 8.84–8.90(m,1H), 8.95–9.02(m,1H), 9.60–9.67(m, 1H), 10.25–1047(m,2H)

Pharmaceutical examples of this invention will be given below.

PHARMACEUTICAL EXAMPLE 1

Hard Capsules 25 g of Compound 6 and 7.5 g of polyoxyethylene castor oil dissolved in acetone was mixed with 25 g of silicic anhydride. After the acetone was evaporated, the mixture was further mixed with 5 g of calcium carboxymethylcellulose, 5 g of corn starch, 7.5 g of hydroxypropylcellulose and 20 g of microcrystalline cellulose and 30 ml of water was added thereto, kneaded, dried and then sized. The granules passed through No. 24 mesh screen were capsulated by means of a capsule filling machine so that each capsule can contain 30 mg of Compound 6.

PHARMACEUTICAL EXAMPLE 2

Soft Capsules 50 g of Compound 21 and 130 g of Macrogol 400 were mixed to form a uniform solution. Separately, a gelatin solution comprising 93 g of gelatin, 19 g of glycerol, 10 g of D-sorbitol, 0.2 g of propyl p-hydroxybenzoate and 0.4 g of titanium oxide was prepared which was used as a soft capsule film-forming agent. Soft capsules were prepared using the said solution by means of a manual type flat punching machine to prepare capsules each containing 30 mg of Compound 21.

PHARMACEUTICAL EXAMPLE 3

Injections 0.5 g of Compound 19, an appropriate amount of peanut oil and 1 g of benzyl alcohol were mixed and made a total volume of 100 cc with peanut oil. The resulting solution was poured portionwise into ampoules at 1 cc per ampoule under aseptic manipulation, which were then sealed.

PHARMACEUTICAL EXAMPLE 4

Injections 0.5 g of Compound 4, 5.0 g of hydrogenated castor oil polyoxyethylene-(60)-ether (Nikkol HCO 60 manufactured by Nikko Chemicals Co.), 20 g of propylene glycol, 10 g of glycerol and 5.0 g of ethanol were mixed and 100 ml of distilled water was added and stirred. The solution was poured portionwise into ampoules at 1.4 ml per ampoule under aseptic manipulation, which were then sealed.

PHARMACEUTICAL EXAMPLE 5

Lipid Emulsions

To 10 g of purified soybean oil was added 30 mg of Compound 6 and the mixture was dissolved by warming. To the resulting solution were added 1.2 g of purified egg yolk phospholipid and 2.5 g of glycerol and the mixture was dissolved by warming while vigorously stirring and then an appropriate volume of distilled water was added. The mixture was stirred by means of Polytron Homogenizer (trade name, sold by KINEMATICA AG) to prepare a crude emulsion. The crude emulsion was further emulsified under elevated pressure by means of a microfluidics homogenizer and was made to 100 ml by the addition of distilled water to prepare an extremely fine lipid emulsion. The average diameter of dispersed fat particles in the lipid emulsion was 0.2–0.3μ and no particles having the diameter of not less than 1μ were contained.

PHARMACEUTICAL EXAMPLE 6

Lipid Emulsions

To 10 g of purified soybean oil was added 110 mg of Compound 2 and the mixture was dissolved by warming. To the resulting solution were added 1.2 g of purified egg yolk phospholipid and 2.5 g of glycerol and the mixture was dissolved by warming while vigorously stirring and then an appropriate volume of distilled water was added. The mixture was stirred by means of Polytron Homogenizer to prepare a crude emulsion. The crude emulsion was further emulsified under elevated pressure by means of a microfluidics homogenizer and was made to 100 ml by the addition of distilled water to prepare an extremely fine lipid emulsion. The average diameter of dispersed fat particles in the lipid emulsion was 0.2–0.3μ and no particles having the diameter of not less than 1μ were contained.

PHARMACEUTICAL EXAMPLE 7

Lipid Emulsions

To 10 g of purified soybean oil was added 30 mg of Compound 6 and the mixture was dissolved by warming. To the solution were added 1.2 g of purified egg yolk phospholipid and 6.5 g of D-sorbitol and the mixture was dissolved by warming while vigorously stirring and then an appropriate volume of distilled water was added. The mixture was stirred by means of Polytron Homogenizer to prepare a crude emulsion. The crude emulsion was further emulsified under elevated pressure by means of a microfluidics homogenizer and was made to 100 ml by the addition of distilled water to prepare an extremely fine lipid emulsion. The average diameter of dispersed fat particles in the lipid emulsion was 0.2–0.3μ and no particles having the diameter of not less than 1μ were contained.

PHARMACEUTICAL EXAMPLE 8

Lipid Emulsions

To 10 g of purified soybean oil was added 30 mg of Compound 1 and the mixture was dissolved by warming. To the resulting solution were added 1.2 g of purified soybean phospholipid and 2.5 g of glycerol and the mixture was dissolved by warming while vigorously stirring and then an appropriate volume of distilled water was added. The mixture was stirred by means of Polytron Homogenizer to prepare a crude emulsion. The crude emulsion was further emulsified under elevated pressure by means of a microfluidics homogenizer and was made to 100 ml by the addition of distilled water to prepare an extremely fine lipid emulsion. The average diameter of dispersed fat particles in the lipid emulsion was 0.2–0.3$\mu$ and no particles having the diameter of not less than 1$\mu$ were contained.

PHARMACEUTICAL EXAMPLE 9

Lipid Emulsions

To 5 g of purified soybean oil and 5 g of MCT was added 10 mg of Compound 21 and the mixture was dissolved by warming. To the resulting solution were added 0.6 g of purified soybean phospholipid and 0.6 g of purified egg yolk phospholipid and the mixture was dissolved by warming while vigorously stirring and then an appropriate volume of distilled water was added. The mixture was stirred by means of Polytron Homogenizer to prepare a crude emulsion. The crude emulsion was further emulsified under elevated pressure by means of a microfluidics homogenizer and was made to 100 ml by the addition of distilled water to prepare an extremely fine lipid emulsion. The average diameter of dispersed fat particles in the lipid emulsion was 0.2–0.3$\mu$ and no particles having the diameter of not less than 1$\mu$ were contained.

PHARMACEUTICAL EXAMPLE 10

Lipid Emulsions

The same procedure as described in Pharmaceutical Example 3 was carried out except that 50 mg of sodium palmitate and 50 mg of phosphatidic acid were further added, thereby forming 100 ml of the lipid emulsion containing 30 mg of Compound 6. The average diameter of dispersed fat particles in the lipid emulsion was 0.2–0.3$\mu$ and no particles having the diameter of not less than 1$\mu$ were contained.

The effect of the drugs containing the present isoprenylamine derivatives will be illustrated below by way of the test examples.

In these tests, GPT (glutamic-pyruvic transaminase) and GOT (glutamic-oxaloacetic transaminase) were determined using kits for the determination of GPT and GOT upon the method by U. Lippi et al., Iatrozyme TA-Lq (available from Iatron Laboratories Inc.), wherein the NADH formed when enzymes act upon substrates can reduce nitrotetrazolium blue (NTB) via 1-methoxy-5-methylphenazinium methylsulfate (1-methoxy PMS) to form formazan, which is then subjected to colorimetric analysis at a wavelength of 560 nm.

TEST EXAMPLE 1
Inhibitory Action on Hepatopathy in Hepatopathy Models by Carbon Tetrachloride
Test Method Inhibitory action of lipid emulsions containing the present isoprenylamine derivatives was evaluated by inhibition rates of GPT and GOT in experimental hepatopathy models prepared by administering carbon tetrachloride.

The experimental hepatopathy model was prepared by introperitoneal administration of 0.02 ml/kg carbon tetrachloride to ddY strain male mice (6 weeks old, body weight of about 30 g). Carbon tetrachloride was diluted with olive oil to a concentration of 0.5% when administered.

The present isoprenylamine derivatives were formulated into the lipid emulsions according to the method described in Pharmaceutical Example 8 and intravenously administered at a dose of 0.1–10 $\mu$g/kg one hour before the administration of carbon tetrachloride.

20 hours after the administration of carbon tetrachloride, blood samples were collected from animals under ether anesthesia and centrifuged. Then, serum GPT and GOT were determined and the respective inhibition rates were calculated on the bases of the serum GPT and GOT values obtained when the present isoprenylamine derivative was not administered being defined as 100, respectively.

The GPT and GOT inhibition rates of the present isoprenylamine derivatives are shown in Table 1, respectively.

TABLE 1

| Compound No. | Dose ($\mu$g/kg) | GPT inhibition (%) | GOT inhibition (%) |
| --- | --- | --- | --- |
| Compound 1  | 1   | 21 | 13 |
| Compound 4  | 1   | 22 | 28 |
| Compound 6  | 1   | 40 | 50 |
| Compound 7  | 1   | 42 | 42 |
| Compound 8  | 10  | 22 | 25 |
| Compound 13 | 0.1 | 21 | 14 |
| Compound 15 | 10  | 24 | 18 |
| Compound 19 | 1   | 31 | 43 |
| Compound 20 | 0.1 | 60 | 53 |
| Compound 21 | 1   | 33 | 38 |

TEST EXAMPLE 2
Inhibitory Action on Hepatopathy in Hepatopathy Models by Carbon Tetrachloride
Test Method Inhibitory actions of the present isoprenylamine derivatives was evaluated by inhibition rates of GPT and GOT in experimental hepatopathy models prepared by administering carbon tetrachloride.

The experimental hepatopathy model was prepared by intraperitoneal administration of 0.02 ml/kg carbon tetrachloride to ddY strain male mice (6 weeks old, body weight of about 30 g). Carbon tetrachloride was diluted with olive oil to a concentration of 0.5% when administered.

Compound 6 was formulated to a suspension with 2% Tween 80 and intravenously administered at a dose of 0.1 mg/kg one hour before the administration of carbon tetrachloride.

20 hours after the administration of carbon tetrachloride, blood samples were collected from animals under ether anesthesia and centrifuged. Then, serum GPT and GOT were determined and the respective inhibition rates were calculated on the bases of the serum GPT and GOT values obtained when Compound 6 was not administered being defined as 100, respectively.

The GPT and GOT inhibition rates of Compound 6 are shown in Table 2, respectively.

TABLE 2

| Compound No. | Dose (mg/kg) | GPT inhibition (%) | GOT inhibition (%) |
| --- | --- | --- | --- |
| Compound 6 | 0.1 | 34 | 37 |

TEST EXAMPLE 3

Inhibitory Action on Hepatopathy in Hepatopathy Models by D-galactosamine

Test Method

Inhibitory action of lipid emulsions containing the present isoprenylamine derivatives was evaluated by inhibition rates of GPT and GOT in experimental hepatopathy models prepared by D-galactosamine administration.

The experimental hepatopathy model was prepared by intraperitoneal administration of D-galactosamine at 400 mg/kg to Wistar strain male mice weighing about 170 g. The present isoprenylamine derivative was formulated to a lipid emulsion according to the method described in Pharmaceutical Example 8, and was intravenously administered at a dose of 10–30 μg/kg 2 hours after the administration of D-galactosamine.

24 hours after the D-galactosamine administration, blood samples were collected form animals under ether anesthesia and centrifuged. Then, serum GPT and GOT were determined and the respective inhibition rates were calculated on the bases of the serum GPT and GOT values obtained when the present isoprenylamine derivatives were not administered being defined as 100, respectively.

For comparison, glycyrrhizin ammonium (Tokyo Kasei Co.) dissolved in distilled water was administered in a similar manner to that for the isoprenylamine derivatives, blood sampling and determination were conducted and the serum GPT and GOT inhibition rates were calculated.

The GPT and GOT inhibition rates of the present isoprenylamine derivatives and glycyrrhizin ammonium are shown in Table 3.

TABLE 3

| Compound No. | Dose (μg/kg) | GPT inhibition (%) | GOT inhibition (%) |
|---|---|---|---|
| Compound 2 | 10 | 23 | 23 |
| Compound 3 | 10 | 20 | 21 |
| Compound 4 | 10 | 30 | 31 |
| Compound 5 | 10 | 27 | 29 |
| Compound 6 | 10 | 40 | 40 |
| Compound 9 | 30 | 53 | 47 |
| Compound 10 | 30 | 63 | 54 |
| Compound 11 | 30 | 55 | 41 |
| Compound 12 | 30 | 53 | 42 |
| Compound 14 | 30 | 64 | 55 |
| Compound 16 | 30 | 43 | 48 |
| Compound 17 | 30 | 23 | 24 |
| Compound 18 | 30 | 20 | 22 |
| Compound 20 | 10 | 43 | 44 |
| Compound 24 | 30 | 25 | 30 |
| Compound 25 | 30 | 30 | 32 |
| Compound 26 | 30 | 35 | 40 |
| Glycyrrhizin ammonium | 3000 | 25 | 22 |

TEST EXAMPLE 4

Study on Toxicity

Toxicity of the lipid emulsion containing the isoprenylamine derivatives was studied by the following test.

To 6-week old ddY strain male mice weighing about 30 g was intravenously administered the lipid emulsion prepared according to the method described in Pharmaceutical Example 8, using the present isoprenylamine derivatives as indicated in the Table 1 at a dose of 1000 μg/kg. No mortality was observed in every case.

The present isoprenylamine derivatives have an extremely low toxicity and a high safety, as apparent from this Test Example.

The present isoprenylamine derivatives, in view of the properties as a prophylactic or therapeutic agent for hepatic diseases, will often have to be continuously administered over a prolonged period of time and they may also be very useful in this respect.

A prophylactic and therapeutic agent for hepatic diseases comprising the isoprenylamine derivatives represented by the above general formula (II) according to this invention, as well as a prophylactic or therapeutic agent for hepatic diseases comprising a lipid emulsion comprising the said isoprenylamine derivatives can exert a satisfactory inhibitory action on hepatopathy at a lower dose.

Accordingly, it is very clinically useful as a prophylactic or therapeutic agent for hepatic diseases with the advantages of lowered doses, reduced side effects and others.

We claim:

1. An isoprenylamine compound represented by the formula (I):

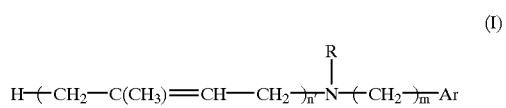

(I)

wherein n' represents an integer from 11 to 12, m represents an integer from 0 to 3, Ar represents a phenyl group, a furyl group, a thienyl group or a pyridyl group, said group being optionally substituted with one or more of an alkyl group of 1 to 4 carbon atoms, an alkoxy group of 1 to 4 carbon atoms, a methylenedioxy group, a hydroxy group or a halogen atom, and R represents a hydrogen atom or an alkyl group of 1 to 4 carbon atoms;

or a pharmacologically acceptable salt thereof.

2. The isoprenylamine compound of claim 1, wherein n' is 11.

3. The isoprenylamine compound of claim 1, wherein n' is 12.

4. The isoprenylamine compound of claim 1, wherein Ar is unsubstituted.

5. The isoprenylamine compound of claim 1, wherein Ar is substituted.

6. The isoprenylamine compound of claim 1, wherein R is hydrogen.

7. A pharmaceutical composition which comprises an isoprenylamine compound or a pharmacologically acceptable salt thereof as claimed in claim 1 and a pharmaceutically acceptable carrier.

8. A lipid emulsion which comprises an isoprenylamine compound represented by formula (II):

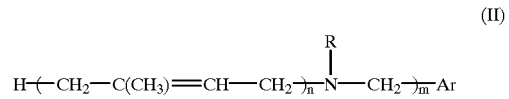

(II)

wherein n represents an integer from 4 to 12, m represents an integer from 0 to 3, Ar represents a phenyl group, a furyl group, a thienyl group or a pyridyl group, said group being optionally substituted with one or more of an alkyl group of 1 to 4 carbon atoms, an alkoxy group of 1 to 4 carbon atoms, a methylenedioxy group, a hydroxy group or a halogen atom, and R represents a hydrogen atom or an alkyl group of 1 to 4 carbon atoms;

or a pharmacologically acceptable salt thereof.

9. A lipid emulsion as claimed in claim 8, wherein n is 9, 10 or 11, m is 1, R is hydrogen or methyl, and Ar is a phenyl, 3,4-methylenedioxyphenyl, 3,4-dihydroxyphenyl or 4-hydroxy-3-methoxyphenyl group.

10. A lipid emulsion as claimed in claim 8, wherein said lipid emulsion comprises:
   (a) 0.0001–1% (w/v) of the isoprenylamine compound represented by formula (II) or a pharmacologically acceptable salt thereof,
   (b) 5–50% (w/v) of at least one of lipid emulsion base selected from the group consisting of vegetable oils, triglycerides of medium chain fatty acids having 8 to 12 carbon atoms and di- and mono-glycerides of fatty acids having 6 to 18 carbon atoms,
   (c) 0.05–25% (w/v) of at least one of emulsifying agent selected from the group consisting of phospholipids and nonionic surface active agents, and
   (d) water.

11. A lipid emulsion as claimed in claim 10, wherein said vegetable oil is soybean oil.

12. A lipid emulsion as claimed in claim 10, wherein said phospholipid is egg yolk phospholipid or soybean phospholipid.

13. A lipid emulsion as claimed in claim 10, further comprising at least one isotonic agent selected from the group consisting of glycerol, sugar alcohols, monosaccharides, disaccharides and amino acids.

14. A lipid emulsion as claimed in claim 10, further comprising at least one emulsifying aid selected from the group consisting of aliphatic acids having 6 to 22 carbon atoms and pharmacologically acceptable salts thereof, phosphatidylethanolamine, phosphatidylserine and stearylamine.

15. A lipid emulsion as claimed in claim 10, further comprising at least one stabilizer selected from the group consisting of cholesterol, tocopherol and phosphatidic acid.

16. A lipid emulsion as claimed in claim 10, further comprising at least one stabilizer selected from the group consisting of albumin and fatty acid amide derivatives thereof and polysaccharides and fatty acid ester derivatives thereof.

17. A method for treating hepatic diseases which comprises administering to patients in need thereof an isoprenylamine compound represented by formula (II):

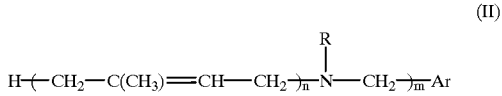

(II)

wherein
   n represents an integer from 4 to 12,
   m represents an integer from 0 to 3,
   Ar represents a phenyl group, a furyl group, a thienyl group or a pyridyl group, said group being optionally substituted with one or more of an alkyl group of 1 to 4 carbon atoms, an alkoxy group of 1 to 4 carbon atoms, a methylenedioxy group, a hydroxy group or a halogen atom, and
   R represents a hydrogen atom or an alkyl group of 1 to 4 carbon atoms;

or a pharmacologically acceptable salt thereof, at a daily dose of 0.01 to 500 µg/kg.

18. A method for treating hepatic diseases as claimed in claim 17, wherein n is 9, 10 or 11, m is 1, R is hydrogen or a methyl group, Ar is a phenyl, 3,4-methylenedioxyphenyl, 3,4-dihydroxyphenyl or 4-hydroxy-3-methoxyphenyl group.

19. A method for treating hepatic diseases as claimed in claim 17, wherein the compound of the formula (II) or a pharmacologically acceptable salt thereof is administered in the form of a lipid emulsion.

20. A method for treating hepatic diseases as claimed in claim 17, wherein said lipid emulsion comprises:
   (a) 0.0001–1% (w/v) of said isoprenylamine compound represented by formula (II) or a pharmacologically acceptable salt thereof,
   (b) 5–50% (w/v) of at least one of lipid emulsion base selected from the group consisting of vegetable oils, triglycerides of medium chain fatty acids having 8 to 12 carbon atoms and di- and mono-glycerides of fatty acids having 6 to 18 carbon atoms,
   (c) 0.05–25% (w/v) of at least one of emulsifying agent selected from the group consisting of phospholipids and nonionic surface active agents, and
   (d) water,
and the daily dose of the compound of formula (II) is 0.01 to 100 µg/kg.

21. A method for treating hepatic diseases, comprising administering to a patient in need thereof an effective amount of an isoprenylamine compound represented by formula (II):

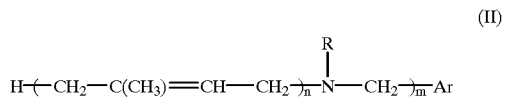

(II)

wherein
   n represents an integer from 4 to 12,
   m represents an integer from 0 to 3,
   Ar represents a phenyl group, a furyl group, a thienyl group or a pyridyl group, said group being optionally substituted with one or more of an alkyl group of 1 to 4 carbon atoms, an alkoxy group of 1 to 4 carbon atoms, a methylenedioxy group, a hydroxy group or a halogen atom, and
   R represents a hydrogen atom or an alkyl group of 1 to 4 carbon atoms;

or a pharmacologically acceptable salt thereof.

22. A method for treating hepatic diseases as claimed in claim 21, wherein n is 9, 10 or 11, m is 1, R is hydrogen or a methyl group, Ar is a phenyl, 3,4-methylenedioxyphenyl, 3,4-dihydroxyphenyl or 4-hydroxy-3-methoxyphenyl group.

23. A method for treating hepatic diseases as claimed in claim 21, wherein the compound of formula (II) or a pharmacologically acceptable salt thereof is administered in the form of a lipid emulsion.

24. A method for treating hepatic diseases as claimed in claim 23, wherein said lipid emulsion comprises:
   (a) 0.0001–1% (w/v) of said isoprenylamine compound represented by formula (II) or a pharmacologically acceptable salt thereof,
   (b) 5–50% (w/v) of at least one of lipid emulsion base selected from the group consisting of vegetable oils, triglycerides of medium chain fatty acids having 8 to 12 carbon atoms and di- and mono-glycerides of fatty acids having 6 to 18 carbon atoms, (c) 0.05–25% (w/v) of at least one of emulsifying agent selected from the group consisting of phospholipids and nonionic surface active agents, and (d) water.

25. The method of claim 21, wherein the daily dose of said isoprenylamine compound represented by formula (II) or a pharmacologically acceptable salt thereof is 0.01 to 100 µg/kg.

26. A method for treating hepatic diseases, comprising administering to a patient in need thereof an effective amount of a the isoprenylamine compound of claim 1 or a pharmacologically acceptable salt thereof.

27. A method for treating hepatic diseases as claimed in claim 26, wherein n is 11, m is 1, R is hydrogen or a methyl group, Ar is a phenyl, 3,4-methylenedioxyphenyl, 3,4-dihydroxyphenyl or 4-hydroxy-3-methoxyphenyl group.

28. A method for treating hepatic diseases as claimed in claim 26, wherein the compound of formula (I) or a pharmacologically acceptable salt thereof is administered in the form of a lipid emulsion.

29. A method for treating hepatic diseases as claimed in claim 27, wherein said lipid emulsion comprises:

(a) 0.0001–1% (w/v) of said isoprenylamine compound represented by formula (I) or a pharmacologically acceptable salt thereof, (b) 5–50% (w/v) of at least one of lipid emulsion base selected from the group consisting of vegetable oils, triglycerides of medium chain fatty acids having 8 to 12 carbon atoms and di- and mono-glycerides of fatty acids having 6 to 18 carbon atoms, (c) 0.05–25% (w/v) of at least one of emulsifying agent selected from the group consisting of phospholipids and nonionic surface active agents, and (d) water.

30. The method of claim 26, wherein the daily dose of said isoprenylamine compound represented by formula (I) or a pharmacologically acceptable salt thereof is 0.01 to 500 µg/kg.

* * * * *